United States Patent
Cooper et al.

(10) Patent No.: US 6,379,720 B1
(45) Date of Patent: Apr. 30, 2002

(54) COMPOSITIONS CONTAINING HOPS EXTRACT AND THEIR USE IN WATER SYSTEMS AND PROCESS STREAMS TO CONTROL BIOLOGICAL FOULING

(75) Inventors: Andrew J. Cooper, Oswego; Anthony W. Dallmier, Aurora, both of IL (US); Howard Raymond Barnes, Cheshire (GB)

(73) Assignee: Nalco Chemical Company, Naperville, IL (US)

( * ) Notice: Subject to any disclaimer, the term of this patent is extended or adjusted under 35 U.S.C. 154(b) by 0 days.

(21) Appl. No.: 09/618,772

(22) Filed: Jul. 18, 2000

(51) Int. Cl.[7] ............................................... A61K 35/78
(52) U.S. Cl. ..................... 424/778; 424/725; 424/405; 424/94.1
(58) Field of Search ................................ 424/405, 725; 422/1; 514/937, 970, 942

(56) References Cited

U.S. PATENT DOCUMENTS

| | | | |
|---|---|---|---|
| 4,010,277 A | * 3/1977 | Swered et al. | |
| 5,082,975 A | 1/1992 | Todd, Jr. et al. | |
| 5,166,449 A | 11/1992 | Todd, Jr. et al. | |
| 5,286,506 A | 2/1994 | Millis et al. | |
| 5,370,863 A | 12/1994 | Barney et al. | |
| 5,385,896 A | * 1/1995 | Bryan et al. | |
| 5,455,038 A | 10/1995 | Barney et al. | |
| 6,080,323 A | * 6/2000 | Yu et al. | |
| 6,090,832 A | * 7/2000 | Bialosky et al. | |
| 6,096,225 A | * 8/2000 | Yang et al. | |
| 6,103,131 A | * 8/2000 | McNeel et al. | |

FOREIGN PATENT DOCUMENTS

DE 0136137 A2 * 4/1985

OTHER PUBLICATIONS

W. J. Simpson et al., Factors affecting antibacterial activity of hop compounds and their derivatives. Journal of Applied Bacteriology 1992, 72, 327–334.
Shigeyuki Mizobuchi et al., Antifungal Activities of Hop Bitter Resins and Related Compounds. Agric. Biol. Chem., 49 (2), 399–403, 1985.
M. Teuber et al., Membrane Leakage in Bacillus subtilis 168 Induced by the Hop Constituents Lupulone, Humulone, Isohumulone and Humulinic Acid. Arch. Mikrobiol. 94, 159–171 (1973).
Pollach et., Einsatz von Hopfernprodukten as Bacteriostaticum in der Zuckerindustrie. Zuckerind. 121 (1996) Nr. 12, S. 919–926.
Walter Hein et al., Neue Erkenntnisse beim Einsatz von Hopfenprodukten in der Zuckerindustrie. Zuckerind. 122, (1997) Nr. 12, S. 940–949.

* cited by examiner

Primary Examiner—Leon B. Lankford, Jr.
Assistant Examiner—Ruth A. Davis
(74) Attorney, Agent, or Firm—Kelly L. Cummings; Thomas M. Breininger

(57) ABSTRACT

Biological fouling is effectively controlled in water systems and process streams through the addition of hops extract.

22 Claims, No Drawings

COMPOSITIONS CONTAINING HOPS EXTRACT AND THEIR USE IN WATER SYSTEMS AND PROCESS STREAMS TO CONTROL BIOLOGICAL FOULING

FIELD OF THE INVENTION

This invention relates generally to biocides and, more particularly, to compositions containing hops extract and their use in water systems and process streams to control biological fouling.

BACKGROUND OF THE INVENTION

Growth of microorganisms such as bacteria, fungi and algae, as well as macroorganisms such as mussels and clams, is problematic in water systems and process streams. As used herein, "water systems" is defined to include municipal, commercial and industrial water systems, as well as aqueous streams. The term "aqueous streams" includes, but is not limited to, streams used for transporting or processing food products and on food surfaces and equipment surfaces that come in contact with the aqueous stream. Examples of food products include fruits vegetables and tubers such as tomatoes, potatoes, bananas, apples, beets, and the like, and meats such as poultry, beef and the like and the surfaces thereof. "Process streams," as used herein includes, but is not limited to, sugar beet diffuser systems.

Proliferation of microorganisms and macroorganisms can cause mechanical, operational and chemical problems with economic and health-related consequences. Similarly, growth of microorganisms in aqueous streams is undesirable. Poor biological control in these systems can cause product spoilage and loss, high water use rates, and the potential for health-related problems.

Many of the chemicals used to control biological fouling in water systems and process streams were developed based on efficacy, without primary emphasis on safety and environmental compatibility. Many of these chemicals are toxic to terrestrial animals or aquatic life, are eye or skin irritants, can produce sensitization reactions with repeated exposure, or have toxic byproducts. There are many naturally-occurring substances with biocidal properties. Natural substances that control microbial fouling have been, to some extent, optimized through evolution and are, by definition, environmentally compatible. Product research and development guided by the use or imitation of natural microbial fouling control substances has the potential to provide useful and innovative water treatment chemistries.

Hops extract is typically produced as an amber colored liquid used primarily for flavor enhancement of beer. Hops extract is obtained from the hop plant (*Humulus lupulus*) as a group of resins, commonly referred to as alpha acids, represented by humulone and its congeners (cohumulone, adhumulone) and beta acids, represented by lupulone and its congeners (colupulone, adlupulone). Beta acid (lupulone) extracts from hops are a product of the brewing process. Hops beta acid extracts are also produced for use in the brewing process to alter properties of the finished beverage. Therefore, abundant sources of raw material for hops extract-based biological control products are available. The fact that hops extract alpha and beta acids are routinely consumed by humans emphasizes the favorable toxicity profile of these substances.

As known in the brewing industry, some hop acids have antimicrobial activity against specific bacteria. For example, U.S. Pat. Nos. 5,082,975 and 5,166,449 disclose that the hop acid hexahydrolupulone inhibits the growth of certain Lactobacillus species. Similarly, U.S. Pat. No. 5,455,038 discloses the use of tetrahydroisohumulone or hexahydrocolupulone to inhibit the growth of Listeria species in food and food packaging materials; U.S. Pat. No. 5,370,863 discloses the use of specific alpha and beta hop acids in oral care compositions for inhibition of microorganisms that cause plaque and periodontal disease; and U.S. Pat. No. 5,286,506 discloses the use of hops extract beta acids to control pathogenic bacteria, such as Listeria, in food.

In general, hops extract is a bacterial inhibitor, not a bactericidal agent. Hops extract has poor efficacy against Gram-negative bacteria which are major slime-producing organisms in many water systems. Hops extract is more effective against Gram-positive bacteria. For example, *Leuconostoc mesenteroides* is a significant problematic microorganism in sugar beet processing and diffuser systems and is a Gram-positive organism which is susceptible to hops extract. Glutaraldehyde and other biocides are currently used in sugar beet diffusion systems to control microbiological fouling due to Leuconostoc and other bacteria. However, none of the biocides currently used in this application, including glutaraldehyde, are as safe as hops extract. The use of hops extract in the sugar industry for microbial control has been previously disclosed (Pollach, et al., Zuckerind. 121 (1996) Nr. 12, S. 919–926; Hein et al., Zuckerind. 122 (1997) Nr. 12, S. 940–949; and Pollach et al., Zuckerind. 124 (1999) Nr. 8, S. 622–637).

Growth of algae can be a problem in any water system exposed to sunlight. Uncontrolled algae growth typically begins as a cosmetic problem, but can lead to problems such as distribution deck plugging and increased halogen demand in cooling towers, and unacceptable water quality in swimming pools, decorative fountain and other water features. Although there are numerous non-oxidizing biocides available for algae control, many of these biocides have high human and environmental toxicity.

Chemistries found naturally or which mimic natural chemical processes are commonly referred to as "green." As environmental restrictions and regulations governing biocides increase, use of some biocides may be restricted. Therefore, green biocides such hops extract may provide an effective and environmentally sound biocide alternative in water treatment.

Accordingly, it would be desirable to provide a method of controlling biological fouling in water systems and process streams using hops extract, a naturally-occurring biological control agent, which is safe and environmentally compatible.

It would also be desirable to provide novel biocidal compositions containing hops extract, in combination with other biocides.

It would furthermore be desirable to provide novel biocidal compositions containing hops extract stabilized with surfactants to prevent hops extract product degradation, separation and precipitate formation prior to application. This surfactant-stabilized hops extract may contain hops extract alone or in combination with other biocides.

SUMMARY OF THE INVENTION

The present invention calls for adding hops extract to a water system or process stream to control biological fouling. Hops extract can be applied with greater safety, convenience and lower environmental impact than currently available biocides.

DETAILED DESCRIPTION OF THE INVENTION

The present invention is directed to a composition and method of controlling biological fouling in water systems and process streams. In accordance with this invention, hops extract is added to the water system or process stream.

As used herein, "hops extract" is defined as extracts which are primarily composed of beta acids, but which may also contain alpha acids. "Beta acids" are defined as lupulone, colupulone, adlupulone, hydrogenated lupulone, hydrogenated colupulone, hydrogenated adlupulone, mixtures thereof and the salts thereof. "Alpha acids" are defined as humulone, cohumulone, adhumulone, hydrogenated humulone, hydrogenated cohumulone, hydrogenated adhumulone, and the isomerized (cis- and trans-) alpha acids, their congeners and their hydrogenated forms, mixtures thereof and the salts thereof.

The biological growth controlled by the method of the present invention may be microbiological or macrobiological in nature. As used herein, "control" is defined to include inhibition, killing and removal. Microbiological growth includes bacteria, fungi, algae and combinations thereof. Macrobiological growth includes, but is not limited to, zebra mussels, blue mussels and the Asiatic clam.

The water systems to which hops extract may be added to control biological fouling include potable waters, cooling waters; food, beverage, and industrial process waters; pulp and paper mill systems; brewery pasteurizers; sweetwater systems; air washer systems; oil field drilling fluids and muds; petroleum recovery processes; industrial lubricants; cutting fluids; heat transfer systems; gas scrubber systems; latex systems; clay and pigment systems; decorative fountains; water intake pipes; ballast water tanks; and ship reservoirs, among others.

The hops extract is added to the water system or process stream by any conventional method at a concentration which effectively controls biological fouling. It is preferred that the amount of hops extract be in the range of about 0.01 ppm to about 10,000 ppm. More preferably, the amount of hops extract is from about 0.05 ppm to about 50 ppm, with about 0.1 to about 10 ppm being most preferred.

Prior to its addition to the water system or process stream, the hops extract may optionally be stabilized with one or more surfactants such as dioctyl sodium sulfosuccinate, sodium mono- and dimethyl naphthalene sulfonates, N-lauroyl sarcosine sodium salt, alkyl polyglycoside and sodium dodecyl diphenyloxide disulfonate. Other surfactant chemistries may also be used and are expected to similarly stabilize hops extracts. Some surfactants that are obvious choices for use in stabilizing hops extract are those surfactants approved by regulatory agencies for indirect or direct food contact or for direct addition to food.

These surfactant and hops extract compositions are intended to illustrate the general invention that hops extracts can be stabilized by adding surfactants. This stabilization inhibits or prevents precipitate formation in the extract and preserves the integrity of the product prior to addition to the water system or process stream. Stabilization of hops extract by use of this invention makes use of hops extract for biological control possible in applications where large hops extract product volumes are required and where hops extract exposed to ambient environmental conditions is stored or used for biological control over extended periods of time.

One or more biocides may be added to the water system or process stream along with the hops extract to control biological fouling. Examples of suitable biocides include 5-chloro-2-methyl-4-isothiazolin-3-one, 2-methyl-4-isothiazolin-3-one, glutaraldehyde, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, alkyldimethylbenzylammonium chloride, dimethyl dialkyl ammonium chloride, poly (oxyethylene(dimethyliminio)ethylene(diemethyliminio) ethylene dichloride, methylene bisthiocyanate, 2-decylthioethanamine, tetrakishydroxymethyl phosphonium sulfate, dithiocarbamate, cyanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl)sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis(bromoacetoxy)-2-butene, bis (tributyltin)oxide, copper sulfate, (2-tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo[2.2.1]heptane-2,3-dicarboxylic acid, 2-(4-thiazolyl)-benzimidazole, orthophenylphenol, 6-ethoxy-1,2-dihydro-2,2,4-trimethyl quinoline and 4,5-dichloro-2-n-octyl-4-isothiazoline-3-one.

The biocides may be added to the water system or process stream by any conventional method. It is preferred that the amount of biocide be in the range of about 0.01 ppm to about 10,000 ppm. More preferably, the amount of biocide is from about 0.05 ppm to about 50 ppm, with about 0.1 ppm to about 10 ppm being most preferred.

The use of hops extract and another biocide in combination surprisingly leads to unexpectedly superior results and allows for significantly less use when utilized in combination, as compared to the amount of each needed individually to achieve the same biocidal performance. This biocidal synergy of the combined hops extract and biocide can be achieved by adding hops extract and a biocide to the water system or process stream simultaneously from individual containers or by applying a single composition that contains both hops extract and biocide.

The present invention provides superior biological fouling control when a composition is added to the water system, or process stream which contains hops extract and at least one biocide selected from the group consisting of 5-chloro-2-methyl-4-isothiazolin-3-one, 2-methyl-4-isothiazolin-3-one, glutaraldehyde, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, alkyldimethylbenzylammonium chloride, dimethyl dialkyl ammonium chloride, poly (oxyethylene(dimethyliminio)ethylene(diemethyliminio) ethylene dichloride, methylene bisthiocyanate, 2-decylthioethanamine, tetrakishydroxymethyl phosphonium sulfate, dithiocarbamate, cyanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl)sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis(bromoacetoxy)-2-butene, bis (tributyltin)oxide, copper sulfate, (2-tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo [2.2.1]heptane-2,3-dicarboxylic acid, 2-(4-thiazolyl)-benzimidazole, orthophenylphenol, 6-ethoxy-1,2-dihydro-2,2,4-trimethyl quinoline and 4,5-dichloro-2-n-octyl-4-isothiazoline-3-one.

It is preferred that the amount of hops extract in the composition be in the range of about 0.1% to about 99% and the amount of biocide be in the range of about 0.1% to about 99%.

The hops extract in the synergistic hops extract/biocide composition may also be stabilized with one or more surfactants to prevent the precipitation of the beta acids over time. Suitable surfactants include, but are not limited to, dioctyl sodium sulfosuccinate, sodium mono- and dimethyl naphthalene sulfonates, N-lauroyl sarcosine sodium salt, alkyl polyglycoside and sodium dodecyl diphenyloxide disulfonate. Other surfactant chemistries may also be used and are expected to similarly stabilize hops extracts. Some surfactants that are obvious choices for use in stabilizing hops extract are those surfactants approved by regulatory agencies for indirect or direct food contact or for direct addition to food.

It is preferred that the amount of hops extract in the composition be in the range of about 0.1% to about 99%, the amount of biocide be in the range of about 0.1% to about 99% and the amount of surfactant be in the range of about 0.1% to about 99%.

The present inventors have surprisingly discovered that biological fouling can be effectively controlled in water systems and process streams through the addition of hops extract. In addition, hops extract can be applied with greater safety, convenience and lower environmental impact than currently available biocides. Moreover, the present invention improves on current technology by demonstrating synergy between hops extract and a wide variety of other biocides. Hops extract and biocides may be used in synergistic combinations to yield better biocidal performance than when hops extract or the biocides are used individually. Hops extract and each biocide may act on target organisms in different ways to cause cell growth inhibition or death. In addition, using a combination of hops extract and one or more biocides allows for application of less total hops extract and/or biocide to achieve a desired level of control. This has safety, environmental and economic advantages. It allows for reduced discharge of potential pollutants, safer application and a more cost effective biological control program.

Safety, as well as low human and environmental toxicities, are some of the primary advantages of the inventive compositions compared to previously described compositions used to control biological fouling. In addition to these primary advantages, the inventive compositions have other benefits such as low volatility and lack of malodors.

Furthermore, this invention provides algicidal and algistatic activities of hops extracts alone and in synergistic compositions with other biocides. The activity of hops extract against algae has not been described previously and was surprising. These compositions are potentially useful in controlling algae in a wide variety of water systems exposed to sunlight and in controlling other organisms that grow in water systems and process streams.

EXAMPLES

The following examples are intended to be illustrative of the present invention and to teach one of ordinary skill how to make and use the invention. These examples are not intended 4to limit the invention or its protection in any way.

Example 1

*Chlorella sorokiniana* and *Scenedesmus obliquus* green algae were grown separately in proteose medium (pH 6.8), harvested by centrifugation and resuspended in proteose medium to concentrate cells. Algae cells were added to 20 ml sterile proteose medium in ten 50 ml PYREX® flasks. Each flask contained a different dilution of hops extract. The hops extract used for these experiments was a ten percent aqueous solution of beta acids. Hops extract concentration in all of the examples is expressed as ppm (beta acids). The number of algae colony forming units per milliliter (CFU/ml) at time zero was determined by plate counts on proteose medium agar plates. The algal population (in CFU/ml) at time zero was $6 \times 10^5$ for the *Chlorella sorokiniana* and $3 \times 10^4$ for the *Scenedesmus obliquus*. Algae cultures were incubated at 25° C. without shaking under grow lights with 16 hour/8 hour light/dark cycles (cool-white fluorescent lamps, 1255 lux) for 14 days. Following incubation, the optical density (OD) at 750 nm (GBC Cintra 5 spectrophotometer, 1 cm light path) and/or adenosine triphosphate (ATP) levels [Nalco TRA-CIDE® method, reported as Relative Light Units (RLU)] of each culture were measured. As shown below in Tables 1 and 2, hops extract beta acids exhibited the ability to inhibit algae growth.

TABLE 1

Inhibition of *Chlorella sorokiniana* growth

| Beta acids (ppm) | Culture OD 750 nm | Percent Inhibition of Growth |
| --- | --- | --- |
| 0 | 0.248 | — |
| 1 | 0.220 | 11 |
| 2 | 0.233 | 6 |
| 4 | 0.222 | 10 |
| 8 | 0.193 | 22 |
| 16 | 0.158 | 36 |
| 32 | 0.119 | 52 |
| 64 | 0.065 | 74 |
| 128 | 0.021 | 92 |

TABLE 2

Inhibition of *Scenedesmus obliquus*

| Beta acids ppm | Culture OD 750 nm | Percent Inhibition of Growth | ATP (RLU) | Percent Inhibition of ATP Production |
| --- | --- | --- | --- | --- |
| 0 | 0.137 | — | 44430 | — |
| 1 | 0.103 | 25 | 38556 | 13 |
| 2 | 0.105 | 23 | 31892 | 28 |
| 4 | 0.109 | 20 | 32893 | 26 |
| 8 | 0.047 | 66 | 18354 | 59 |
| 16 | 0.002 | 99 | 1112 | 97 |
| 32 | 0.002 | 99 | 882 | 98 |
| 64 | 0.004 | 97 | 802 | 98 |

Example 2

100 ul pure culture algae (*Chlorella sorokiniana* or *Scenedesmus obliquus* green algae at $10^7$ CFU/ml) in synthetic cooling water (pH 8.2) were added to 200 ul hops extract dilutions in synthetic cooling water in microplate (FALCON® 3075) wells. Microplates were covered with the provided lid and incubated at 25° C. for six days with 16 hour/8 hour light/dark cycles (cool-white fluorescent lamps, 1255 lux). Following incubation, supernatant was removed from each microplate well by vacuum aspiration. Algae cells remained attached to the bottom of each well. 200 ul of dimethylsulfoxide (DMSO) were added to each microplate well to dissolve algae cells and extract chlorophyll. The optical density at 650 nm of each extraction was determined by a microplate reader (Beckman Biomek®). The optical density (absorbance at 650 nm) of each extraction correlated with the amount of chlorophyll in each algal aliquot following incubation with hops extract. Decreased chlorophyll indicates algicidal activity. As shown below in Table 3, hops extract exhibited the ability to kill algae.

TABLE 3

Algicidal activity against *Chlorella sorokiniana* and *Scenedesmus obliquus*

| Ppm beta acids | *Chlorella sorokiniana* | *Scenedesmus obliquus* |
|---|---|---|
| 0 | 0.48 | 0.52 |
| 4 | 0.46 (4) | 0.50 (4) |
| 8 | 0.45 (6) | 0.47 (10) |
| 16 | 0.43 (10) | 0.40 (23) |
| 32 | 0.39 (19) | 0.21 (60) |
| 64 | 0.18 (63) | 0.17 (67) |
| 128 | 0.08 (83) | 0.13 (75) |
| 256 | 0.06 (88) | 0.12 (77) |

*( ) = percent reduction in OD 650 nm of chlorophyll extraction compared to untreated control.

Example 3

Synergism refers to a case in which the performance of two or more active ingredients is improved relative to the sum of their individual performances. The accepted method used to determined synergism is described by Kull, F. C., Eisman, P. C., Sylwestrowicz, H. D., and Mayer, R. L. in *Applied Microbiology* 9:538–541 (1961), and is well known in the art.

The equation for determining synergism is as follows:

$$Q_a Q_A + Q_b/Q_B = \text{Synergism Index (SI)}$$

Where $Q_A$ and $Q_B$ are the concentrations of compounds A or B that produce an endpoint when acting alone, and where $Q_a$ and $Q_b$ are the concentrations of compounds A or B acting in the A/B combination required to produce an endpoint. The endpoint is defined by the particular test method, for example, an optical density.

To determine synergism, one evaluates the Synergism Index (SI). Where SI is less than 1, the performance of the mixture is superior to the sum of the individual performances and synergism exists.

The efficacy of the invention was tested in the following manner:

*Scenedesmus obliquus* green algae cells were prepared in synthetic cooling water (pH 8.2) to a concentration of $10^7$ CFU/ml. 100 ul of the algae suspension were added to 200 ul aliquots of hops extract antimicrobial compositions in synthetic cooling water contained in 96 well microplates (FALCON® 3075). A wide range of hops extract/biocide combinations were tested. Microplates were covered with the provided lid and incubated at 25° C. for six days with 16 hour/8 hour light/dark cycles (cool-white fluorescent lamps, 1255 lux). Following incubation, supernatant was removed from each microplate well by vacuum aspiration. Algae cells remained attached to the bottom of each microplate well. 200 ul of dimethylsulfoxide (DMSO) were added to each microplate well to dissolve the algae cells and extract chlorophyll. The optical density at 650 nm of each extraction was determined using a plate reader (Beckman Biomek®). The optical density of each extraction correlated with the amount of chlorophyll in each algae aliquot following incubation with hops extract compositions.

Synergistic compositions were made by mixing hops extract with each of the following compounds: methylchloro/isothiazolone ("IZN"), poly(oxyethylene (dimethyliminio)ethylene(dimethyliminio)ethylene dichloride) ("POLYQUAT"), glutaraldehyde ("GLUT"), 2-(tert-butylamino)-4-chloro-6(ethylamino)-s-triazine ("TBTZ"), 4,5-dichloro-2-n-octyl-4-isothiazolin-3-one ("DCOI"), tetrakishydroxymethyl phosphonium sulfate ("THPS"), 2-(2-bromo-2-nitroethenyl)furan ("BNEF"), 2,2-dibromo-3-nitrilopropionamide ("DBNPA"), and 2-(decylthio)ethanamine ("DTEA") in water at room temperature. A wide range of ratios of the two active ingredients can be used, depending on several factors including the microorganisms to be controlled. In this example, data designated as $Q_A$ and $Q_a$ in each case are for hops extract and data designated as $Q_B$ and $Q_b$ are for the other antimicrobial (IZN, POLYQUAT, GLUT, TBTZ, DCOI, THPS, BNEF, DBNPA, and DTEA).

Table 4 illustrates synergistic combinations of hops extract with other antimicrobials. A wide range of combinations were tested systematically until synergistic compositions were discovered. The antimicrobial compositions shown below exhibit synergistic activity with respect to green algae. However, the examples disclosed herein should not be considered to disclose all possible microorganisms which may be controlled by the synergistic combinations, nor should the identified ranges be viewed as limiting in nature. All synergistic antimicrobial combinations of the identified ingredients are intended to be within the scope of the present invention, and all antimicrobial uses thereof are intended to be claimed.

TABLE 4

| Antimicrobial | $Q_A$ | $Q_B$ | $Q_a$ | $Q_b$ | SI | $Q_a:Q_b$ |
|---|---|---|---|---|---|---|
| IZN[2] | >256 (512)[1] | >16 (32) | 256 | 8 | 0.75 | 32:1 |
|  |  |  | 128 | 8 | 0.50 | 16:1 |
|  |  |  | 64 | 8 | 0.38 | 8:1 |
|  |  |  | 128 | 16 | 0.75 | 8:1 |
|  |  |  | 64 | 16 | 0.63 | 4:1 |
|  |  |  | 32 | 16 | 0.56 | 2:1 |
|  |  |  | 16 | 16 | 0.53 | 1:1 |
| POLYQUAT[3] | 256 | >16 (32) | 64 | 4 | 0.38 | 16:1 |
|  |  |  | 128 | 8 | 0.75 | 16:1 |
|  |  |  | 64 | 8 | 0.50 | 8:1 |
| GLUT[4] | 32 | >16 (32) | 16 | 4 | 0.63 | 4:1 |
| TBTZ[5] | 32 | 16 | 16 | 0.5 | 0.53 | 8:1 |
|  |  |  | 16 | 4 | 0.75 | 4:1 |
| DCOI[6] | 256 | >16 (32) | 128 | 0.5 | 0.52 | 256:1 |
|  |  |  | 128 | 1 | 0.53 | 128:1 |
|  |  |  | 128 | 2 | 0.56 | 64:1 |
|  |  |  | 128 | 4 | 0.63 | 32:1 |
|  |  |  | 128 | 8 | 0.75 | 16:1 |
|  |  |  | 64 | 8 | 0.50 | 8:1 |
|  |  |  | 64 | 16 | 0.75 | 4:1 |
|  |  |  | 4 | 16 | 0.52 | 1:4 |
| THPS[7] | 32 | 16 | 8 | 4 | 0.50 | 2:1 |
|  |  |  | 4 | 4 | 0.38 | 1:1 |
|  |  |  | 8 | 8 | 0.75 | 1:1 |
| BNEF[8] | 32 | >16 (32) | 16 | 1 | 0.53 | 16:1 |
|  |  |  | 8 | 16 | 0.75 | 1:2 |
|  |  |  | 4 | 16 | 0.63 | 1:4 |
| DBNPA[9] | 64 | >16 (32) | 16 | 16 | 0.75 | 1:1 |
|  |  |  | 4 | 16 | 0.56 | 1:4 |
| DTEA[10] | 32 | 16 | 16 | 1 | 0.56 | 16:1 |
|  |  |  | 16 | 2 | 0.63 | 8:1 |
|  |  |  | 4 | 2 | 0.25 | 2:1 |
|  |  |  | 8 | 4 | 0.50 | 2:1 |
|  |  |  | 8 | 8 | 0.75 | 1:1 |
|  |  |  | 4 | 8 | 0.63 | 1:2 |

[1]( ) in columns $Q_A$ and $Q_B$ = the antimicrobial concentration in ppm used for synergy calculations when the highest concentration tested did not produce an OD650 lower than the endpoint OD650.
[2]Endpoint OD650 = 0.100
[3]Endpoint OD650 = 0.150
[4]Endpoint OD650 = 0.250

TABLE 4-continued

| Antimicrobial | $Q_A$ | $Q_B$ | $Q_a$ | $Q_b$ | SI | $Q_a:Q_b$ |
|---|---|---|---|---|---|---|

[5]Endpoint OD650 = 0.250
[6]Endpoint OD650 = 0.150
[7]Endpoint OD650 = 0.250
[8]Endpoint OD650 = 0.300
[9]Endpoint OD650 = 0.200
[10]Endpoint OD650 = 0.300

Example 4

When packaging hops extract, a container is filled with the product and sealed immediately, or it may be packaged in an atmosphere, such as nitrogen, other than the ambient air environment. Upon opening such a product container and exposing to ambient air, precipitate formation within the hops extract product is frequently observed within a few days. All of the product in the container must be used prior to precipitate formation. If product is not used prior to this time, hops extract quality and effectiveness are compromised and the product may be rendered useless. Additionally, the container itself may be damaged due to collection of insoluble hops extract precipitates and the container may be rendered useless. Table 5 illustrates newly invented compositions containing hops extract and surfactants in which precipitate formation was inhibited. Freshly prepared hops beta acid extracts were placed in tubes (Corning® modified polystyrene 15 milliliter sterile centrifuge tubes with caps), to which surfactants were added to the desired concentration (5 milliliter total volume). Tubes were stored unsealed at room temperature in the dark for 72 hours. Following this period, the product in each tube was examined visually for precipitate formation. For each hops extract and surfactant composition, a critical level of surfactant was required to inhibit precipitate formation.

TABLE 5

| Surfactant | Surfactant Active Ingredient Final Concentration (percent) | Hops Extract Beta Acid Concentration (percent) | Precipitate Formation (Yes, Slight, No) |
|---|---|---|---|
| control | 0 | 12.0 | Yes |
| OSS | 10 | 10.3 | No |
| OSS | 5 | 11.1 | No |
| OSS | 1 | 11.8 | Yes |
| MNS | 10 | 6.0 | No |
| MNS | 5 | 9.0 | Slight |
| MNS | 1 | 11.4 | Yes |
| NLS | 10 | 6.0 | No |
| NLS | 5 | 9.0 | No |
| NLS | 1 | 11.4 | Yes |

OSS = dioctyl sodium sulfosuccinate;
MNS = sodium mono- and dimethyl naphthalene sulfonates;
NLS = N-lauroyl sarcosine sodium salt.

In addition to the hops extract/surfactant compositions described above, hops extract compositions were also stabilized using alkyl polyglycoside and sodium dodecyl diphenyloxide disulfonate. Compositions containing 25 percent alkyl polyglycoside or sodium dodecyl diphenyloxide disulfonate and six percent beta acids were stable (no precipitate formation observed) for >80 days. Without the surfactant addition, the same hops extract beta acid preparations formed precipitate within 48 hours.

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

What is claimed is:

1. A method of controlling algal growth in water systems and process streams comprising the step of adding thereto an effective amount of hops extract.

2. The method of claim 1 wherein the hops extract is added to the water system or process stream in an amount from about 0.01 ppm to about 10,000 ppm.

3. The method of claim 1 wherein the hops extract is added to the water system or process stream in an amount from about 0.05 ppm to about 50 ppm.

4. The method of claim 1 wherein the hops extract is added to the water system or process stream in an amount from about 0.1 ppm to about 10 ppm.

5. The method of claim 1 wherein the hops extract is stabilized with at least one surfactant prior to addition.

6. The method of claim 5 wherein the surfactant is selected from the group consisting of dioctyl sodium sulfosuccinate, sodium mono- and dimethyl napthalene sulfonates, N-lauroyl sarcosine sodium salt, alkyl polyglycoside and sodium dodecyl diphenyloxide disulfonate.

7. The method of claim 1 wherein an effective amount of at least one biocide is added to the water system or process stream.

8. The method of claim 7 wherein the biocide is selected from the group consisting of 5-chloro-2-methyl-4-isothiazolin-3-one, 2-methyl-4-isothiazolin-3-one, glutaraldehyde, 2,2-dibromo-3-itrilopropionamide, 2-bromo-2-nitropropane-1,3 diol, 1-bromo-1-(bromomethyl)-1,3-propanedicarbonitrile, etrachloroisophthalonitrile, alkyldimethylbenzylammonium chloride, dimethyl dialkyl ammonium chloride, poly(oxyethylene(dimethyliminio)ethylene(diemethyliminio) ethylene dichloride, methylene bisthiocyanate, 2-decylthioethanamine, tetrakishydroxymethyl phosphonium sulfate, dithiocarbamate, yanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl)sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis(bromoacetoxy)-2-butene, bis(tributyltin)oxide, copper sulfate, (2-tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo[2.2.1]heptane-2,3-dicarboxylic acid, 2-(4-thiazolyl)-benzimidazole, orthophenylphenol, 6-ethoxy-1,2-dihydro-2,2,4-trimethyl quinoline and 4,5-dichloro-2-n-octyl-4-isothiazoline-3-one.

9. The method of claim 7 wherein the biocide is added to the water system or process stream in an amount from about 0.01 ppm to about 10,000 ppm.

10. The method of claim 7 wherein the biocide is added to the water system or process stream in an amount from about 0.05 ppm to about 50 ppm.

11. The method of claim 7 wherein the biocide is added to the water system or process stream in an amount from about 0.1 ppm to about 10 ppm.

12. A method of controlling algal growth in water systems and process streams comprising the step of adding thereto an effective amount of stabilized hops extract.

13. The method of claim 12 wherein the hops extract is stabilized with at least one surfactant.

14. The method of claim 13 wherein the surfactant is selected from the group consisting of dioctyl sodium sulfosuccinate, sodium mono- and dimethyl napthalene sulfonates, N-lauroyl sarcosine sodium salt, alkyl polyglycoside and sodium dodecyl diphenyloxide disulfonate.

15. The method of claim 12 wherein the stabilized hops extract is added to the water system or process stream in an amount from about 0.01 ppm to about 10,000 ppm.

16. The method of claim 12 wherein the stabilized hops extract is added to the water system or process stream in an amount from about 0.05 ppm to about 50 ppm.

17. The method of claim 12 wherein the stabilized hops extract is added to the water system or process stream in an amount from about 0.1 ppm to about 10 ppm.

18. The method of claim 12 wherein an effective amount of at least one biocide is added to the water system or process stream.

19. The method of claim 18 wherein the biocide is selected from the group consisting of 5-chloro-2-methyl-4-isothiazolin-3-one, 2-methyl-4-isothiazolin-3-one, glutaraldehyde, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, alkyldimethylbenzylammonium chloride, dimethyl dialkyl ammonium chloride, poly(oxyethylene(dimethyliminio)ethylene(diemethyliminio)ethylene dichloride, methylene bisthiocyanate, 2-decylthioethanamine, tetrakishydroxymethyl phosphonium sulfate, dithiocarbamate, cyanodithioimidocarbonate, 2-methyl-S-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl)sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis(bromoacetoxy)-2-butene, bis(tributyltin)oxide, copper sulfate, (2-tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo[2.2.1]heptane-2,3-dicarboxylic acid, 2-(4-thiazolyl)-benzimidazole, orthophenylphenol, 6-ethoxy-1,2-dihydro-2,2,4-trimethyl quinoline and 4,5-dichloro-2-n-octyl-4-isothiazoline-3-one.

20. The method of claim 18 wherein the biocide is added to the water system or process stream in an amount from about 0.01 ppm to about 10,000 ppm.

21. The method of claim 18 wherein the biocide is added to the water system or process stream in an amount from about 0.05 ppm to about 50 ppm.

22. The method of claim 18 wherein the biocide is added to the water system or process stream in an amount from about 0.1 ppm to about 10 ppm.

* * * * *